United States Patent [19]

Cheo et al.

[11] 4,208,126
[45] Jun. 17, 1980

[54] SYSTEM FOR DETECTING FOREIGN PARTICLES OR VOIDS IN ELECTRICAL CABLE INSULATION AND METHOD

[75] Inventors: Peter K. Cheo; Arnold J. Cantor, both of West Hartford, Conn.

[73] Assignee: Electric Power Research Institute, Inc., Palo Alto, Calif.

[21] Appl. No.: 909,254

[22] Filed: May 24, 1978

[51] Int. Cl.$^2$ .................... G01N 21/16; G01N 21/32
[52] U.S. Cl. ........................... 356/51; 250/341; 356/73.1; 356/239
[58] Field of Search ............... 356/51, 73.1, 239, 430; 250/562, 563, 572, 341, 338

[56] References Cited

U.S. PATENT DOCUMENTS

| | | | |
|---|---|---|---|
| 3,405,270 | 10/1968 | Briggs | 250/341 |
| 3,586,444 | 6/1971 | Sproul et al. | 356/239 |
| 3,746,575 | 7/1973 | Arnaudin, Jr. et al. | 250/572 |
| 3,777,171 | 12/1973 | Hollenbeck | 356/239 |
| 4,021,217 | 5/1977 | Bondybey et al. | 356/239 |

Primary Examiner—Vincent P. McGraw
Attorney, Agent, or Firm—Flehr, Hohbach, Test

[57] ABSTRACT

A system for detecting foreign particles or voids in the outer insulation jacket of an electrical cable is disclosed herein and utilizes a laser beam of electromagnetic radiation at a given wavelength, preferably within the far-infrared band. This laser is directed into the insulation jacket's cylindrical surface, which must be index-matched with a proper medium such that any portion thereof passing through the insulation jacket unobstructed by voids or foreign matter does so along a predictable primary beam path, and such that any portion impinging a void or foreign particle is caused to scatter along predictable scattering paths including paths which are different than the primary beam path. In this way, at least one detector can be properly aligned in at least one of these different scattering paths for detecting a portion of the scattered radiation, thereby indicating the presence of a void or foreign particle. This system affords a real time, in-process means of inspections of the quality of cable insulation during manufacturing.

22 Claims, 8 Drawing Figures

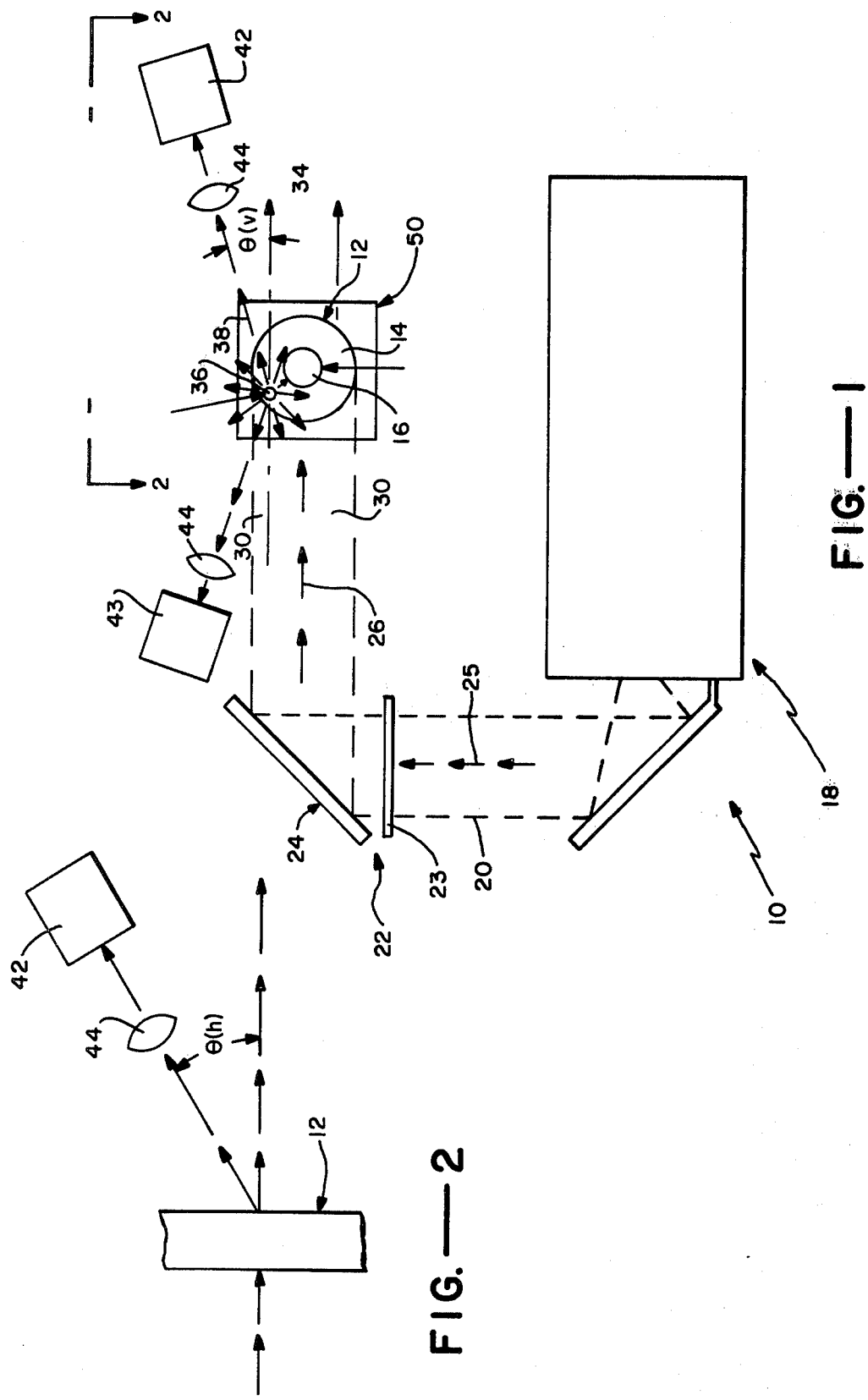

REFRACTION OF FAR INFRARED RAYS IN CABLE INSLUATION
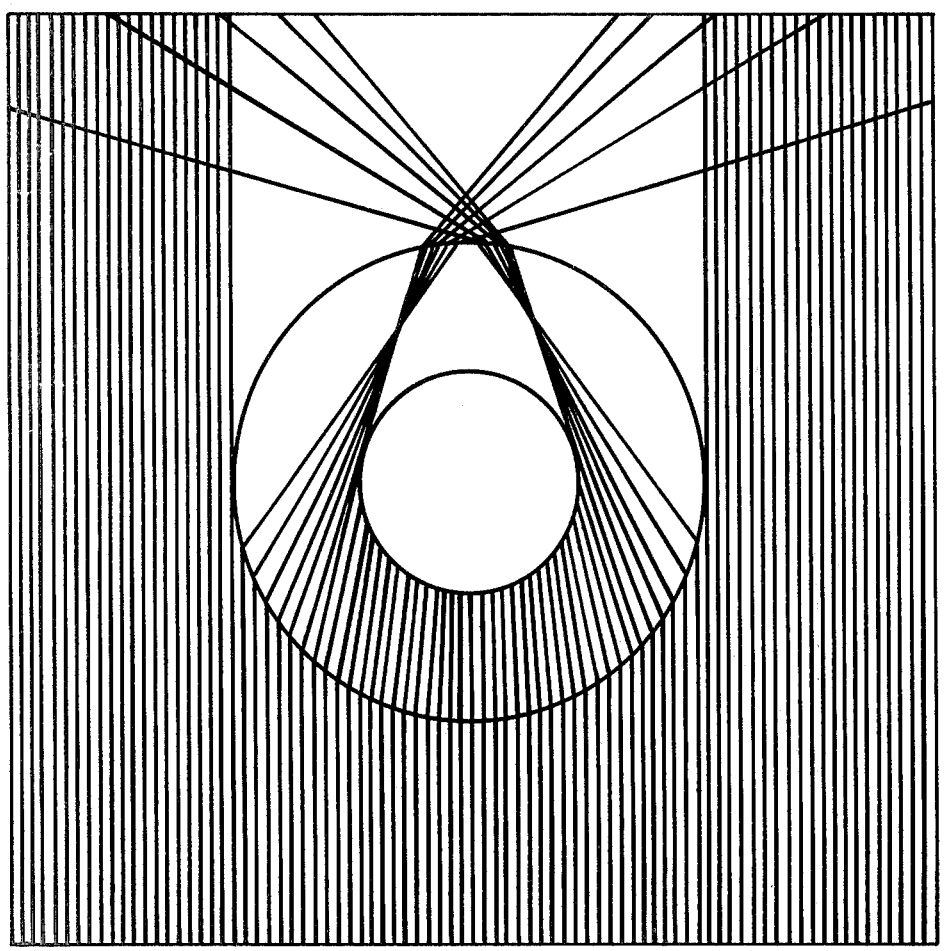
FIG.—3

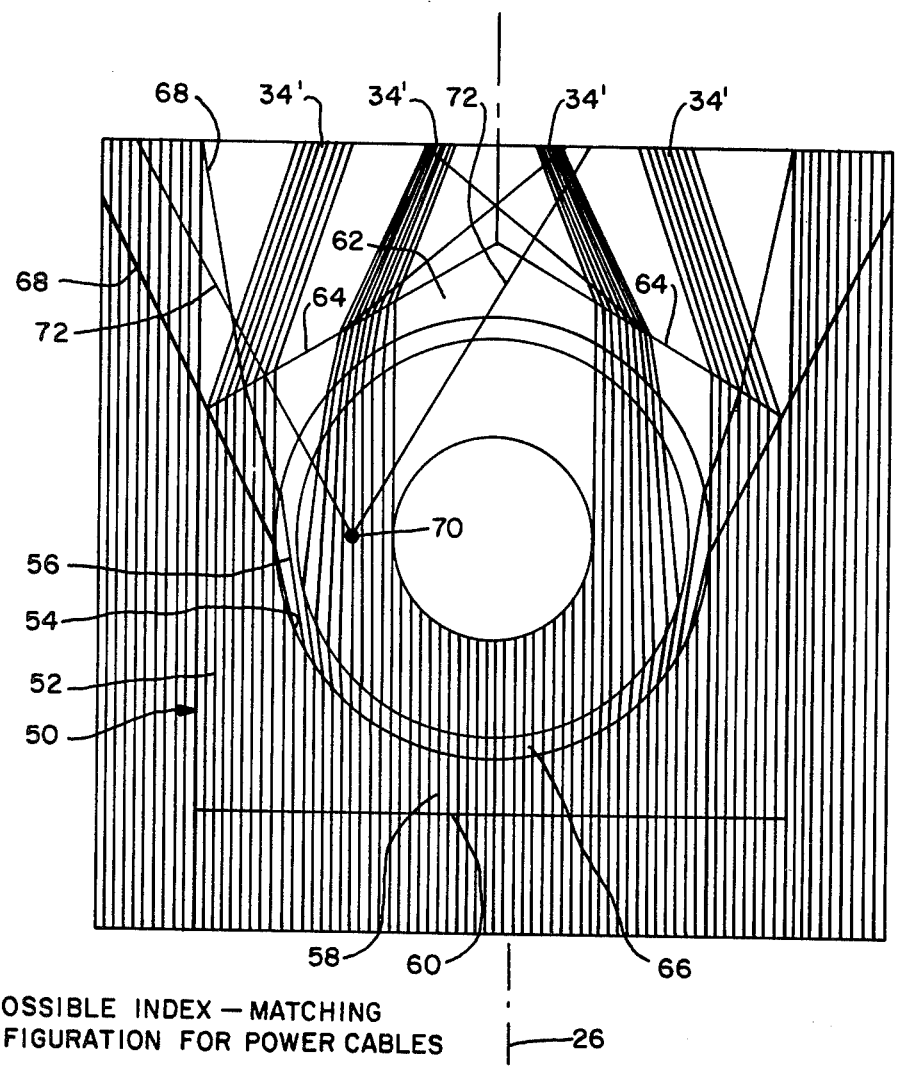
A POSSIBLE INDEX—MATCHING
CONFIGURATION FOR POWER CABLES
FIG.—4
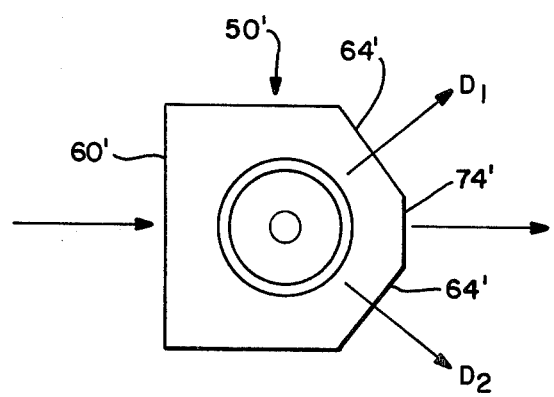
FIG.—5

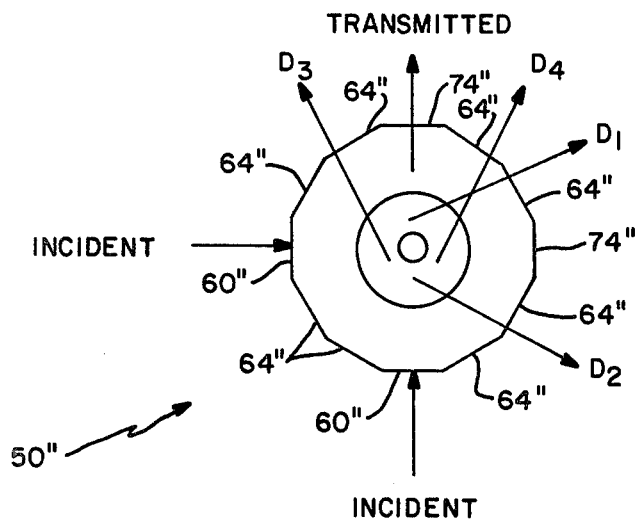
FIG.—6
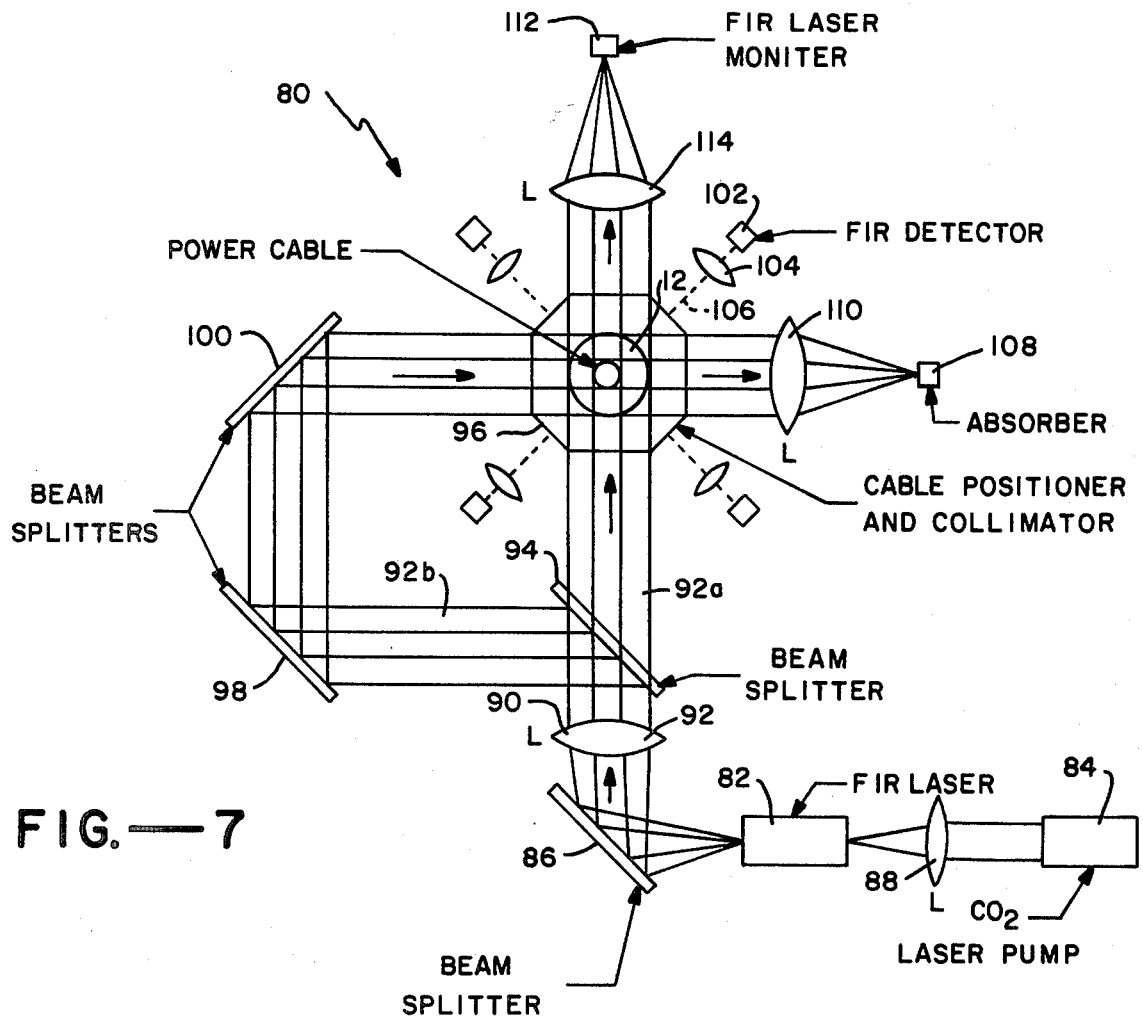
FIG.—7

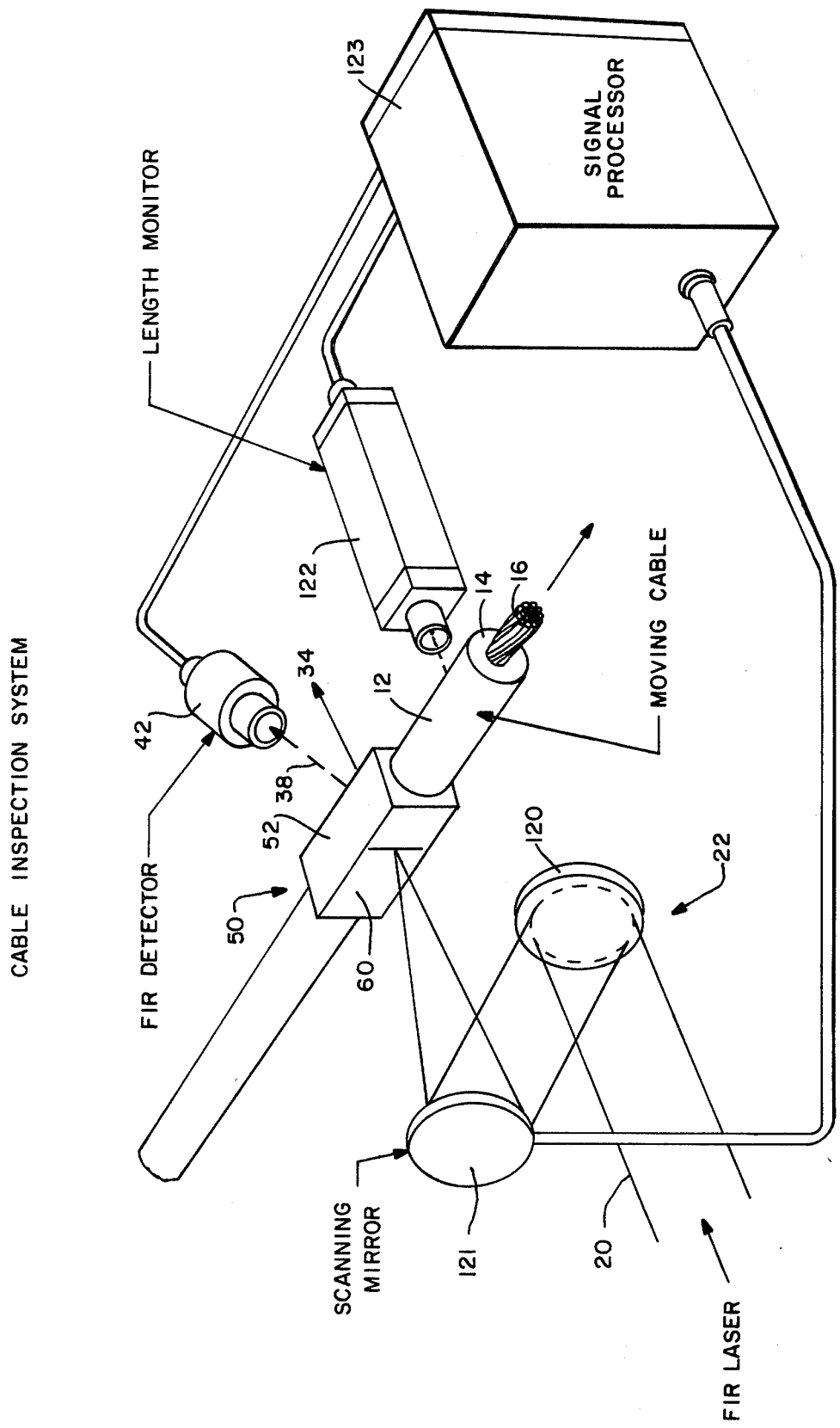

SYSTEM FOR DETECTING FOREIGN PARTICLES OR VOIDS IN ELECTRICAL CABLE INSULATION AND METHOD

BACKGROUND OF THE INVENTION

The present invention relates generally to detection systems as disclosed in co-pending application Ser. No. 909255, filed May 24, 1978, entitled SYSTEM FOR DETECTING PARTICLES OR VOIDS IN PLASTIC MATERIAL AND METHOD (assigned to the assignee of the present application) and more particularly to a system for detecting foreign particles or voids in the outer insulation jacket of an electrical cable, specifically a power cable including a cylindrical insulation jacket constructed of polyethylene material having a predetermined index of refraction and absorption coefficient in a preferred embodiment.

It is well recognized that underground cables for power transmission require insulation coatings which must not only have good electrical properties but also good physical properties so that the cable can withstand the rigors of an underground installation operation and varied environmental conditions in the subsurface area. Commonly used insulating materials include solid plastics such as polyethylene which has many desired physical properties, such as outstanding moisture resistance, high dielectric strength, and extremely low loss characteristics, in addition to many other desired properties.

The use of polyethylene as an extrudable dielectric in high voltage power cables was first recognized in 1945. This recognition occurred as a result of the early usage of polyethylene in voltage coaxial transmission cables for radar systems during the war. The inherent low loss electromagnetic characteristics and high dielectric strength of polyethylene was found to be far superior to that of butyl and oil base compounds. Due to these excellent characteristics, polyethylene has now found extensive usage as the insulator on transmission line cables which are to be buried under ground and operated in excess of 65 kV. The adverse underground environment in conjunction with the high installation expenses in burying the cables, places high and difficult quality control standards on the manufacturing of these cables. At the present time, the desired quality control throughout the industry exceeds the capability of the presently available technology to measure the quality of the product as it is coming off the manufacturing line. This is particularly true of the detection of tiny voids (i.e. bubbles) during the extrusion process. In this regard, the particular polyethylene utilized in underground high voltage cables is especially susceptible to the formation of such voids during the extrusion process and specifically upon cooling. These voids can be electro-active and cause interference as well as premature failures. Such failures are particularly bothersome on high voltage cables which are to be buried underground due to the safety aspects involved and the high cost which is involved in retrieving the cable, repairing it and burying it again.

In the early days (prior to 1948) detection of these voids was crudely accessed by plotting 16 Hz power factor readings against applied voltage and noting the break in which ionization occurred. In 1948, the first Corona level detector was introduced by which the relationship between voids and cable life was established. During the last 20 years, extensive efforts were devoted to the development of a partial discharge detection system by numerous manufacturers. This system is now capable of detecting a single void as small as two (2) mils in diameter with a sensitivity of one (1) picocoulomb on 5000 foot cable lengths. However, detection of voids utilizing this particular system is limited to "clean" voids, which have no foreign gas or other materials inside them.

Recent investigations have since disclosed that the majority of voids appearing in underground high voltage cable during the manufacturing process are not clean under atmospheric pressure. However, as just stated, in the partial discharge detection system the void is required to be clean in order to be detectable, that is, in order for it to break down under applied 60 Hz high voltage and thus generate high-frequency signals capable of detection by present radio techniques. These "unclean voids" also called "internally shielded voids," are equally responsible as clean voids for premature cable failures, particularly failures relating to what is referred to as a "electrochemical treeing phenomena."

It has been established that the typical process for manufacturing this high voltage cable and its environment are in large part responsible for this transformation of clean voids to internally shielded voids, that is, "unclean voids." There are a number of factors which contribute to this conclusion. First, the present manufacturing process relies on water cooling or cross-linking under steam pressure which allows vapor transmission to occlude the void. Second, byproducts given off during the chemical cross-linking process can occlude the void by filling it with a high-pressure gas or a chemical liquid. Finally, permeation or expulsion of water vapor from the voids under low cycling of the cable after installation thereof can also lead to failures.

In addition to the fact that partial discharge detection is not completely satisfactory when required to detect unclean voids, recent studies have indicated that even the most sensitive instruments presently available to underground cable manufacturers are not capable of detecting micro-porosity in the order of two (2) to five (5) micrometers. These micro-porosity voids are not only susceptible to electrochemical treeing, but also precludes cable design and fabrication utilizing the ultimate inherent dielectric break-down capabilities that could be achieved with polyethylene. Furthermore, partial discharge detection can only be conducted as a final test on shielded cable ready for shipment. Hence the presently available instrumentation is not capable of in-process control and considerable scrap results during the manufacturing process because most extruder runs are in the order of 100,000 feet.

As will be seen hereinafter, the present invention is directed to a system for detecting tiny voids as well as contaminants (e.g. foreign particles or unclean voids) and particularly to an in-line system for continuously monitoring the polyethylene insulation jacket as it is extruded into its final shape. In this regard, the presence of solid contaminants contributes equally to premature cable failure and electrochemical treeing, particularly when contaminant boundary does not "wet" the insulation and forms a void therein. Contaminants cannot be detected by the partial discharge measurement techniques (as they are characterized as unclean voids) and the manufacturer must rely on visual assessment by microscopic analysis of, for example, a two-inch specimen for each 10,000 feet of cable, as required by present industry standards. This sample inspection also results in large scrappage and unfortunately it cannot assure the absence of contaminants in the remaining unexamined cable length.

The need for an advancement in the state-of-the-art of the detection of voids and contaminants, regardless of size and internal occulusions, is apparent and must be recognized if the desired service life and ultimate design of polyethylene insulated cable is to be achieved. As stated above, the present invention is directed towards a system capable of in-process detection of voids and contaminants during the manufacturing process without any of the limitatons of the detection systems presently employed. This system uses a laser beam of electromagnetic energy, specifically far-infrared radiation in a preferred embodiment. As will be seen hereinafter, in this preferred embodiment versatility comes mainly from the fact that a host of far-infrared laser transitions are available and can be used to match the void or contaminant sizes of interest. Moreover, it has been specifically found that laser radiation scattering techniques in the far-infrared band is extremely sensitive and permits the detection of one single particle or void in the polyethylene jacket. However, as will also be seen, the system which accomplishes this, in its preferred embodiment, is relatively uncomplicated in design and reliable in use.

OBJECTS AND SUMMARY OF THE INVENTION

One object of the present invention is to provide a system for detecting foreign particles, for example contaminants or voids in the outer insulation jacket of an electrical cable, specifically in the polyethylene insulation jacket of an underground power cable, in a preferred embodiment.

Another object of the present invention is to provide a system which is relatively uncomplicated in design and reliable in use.

Still another object of the present invention is to provide a system which detects "unclean voids" and contaminants (i.e. foreign particles) as well as "clean voids."

Yet another object of the present invention is to provide a system which utilizes a laser scattering technique for detecting the voids and contaminants within the insulation jacket and particularly a system which reliably distinguishes between scattered radiation (from the voids or contaminants) and background radiation (including non-scattered radiation which passes through the insulation jacket).

Still another object of the present invention is to provide a detection system which utilizes a laser beam of electromagnetic radiation and particularly one which accurately and reliably controls the way in which this beam of electromagnetic radiation passes through the insulation jacket so as to reliably discriminate between radiation which passes therethrough in an unobstructed way and radiation which is scattered by a void or foreign particle.

A further object of the present invention is to provide a system of the type recited but one which is especially adaptable for in-line monitoring of the cable insulation jacket as the latter is actually being formed.

Still a further object of the present invention is to provide a method of detecting foreign particles or voids in the outer insulation jacket of an electrical cable utilizing a system of the type described.

As will be discussed in detail hereinafter, the system (or method) disclosed herein utilizes a laser beam of electromagnetic radiation which has a wavelength compatible with the absorption coefficient of the cable insulation jacket for allowing the beam to pass therethrough. This beam of electromagnetic radiation, specifically far-infrared radiation in a preferred embodiment, is directed into the insulation jacket, which is preferably cylindrical, through an index matching medium and along a path incident to and at a predetermined orientation with the overall cable (1) such that any portion of the beam which passes through the insulation jacket unobstructed by voids or foreign matter within the jacket does so along predictable paths and (2) such that any portion which impinges a void or foreign particle is scattered thereby along predictable scattering paths including paths different than the unobstructed paths. In this way, at least one device for detecting electromagnetic radiation at the same wave length can be positioned in alignment with at least one of the different scattering paths for detecting the scattered radiation along that path for indicating the presence (or absence) of a void or foreign particle.

The specific details of this system (or method) will be discussed hereinafter. For the moment, it suffices to say that it utilizes a well controlled beam of electromagnetic radiation and a carefully positioned detector for discriminating between the presence or absence of an internal void or foreign particle in an uncomplicated and yet reliable way.

BRIEF DESCRIPTION OF THE DRAWINGS

FIG. 1 is a diagramatic illustration of a system which is constructed in accordance with the present invention and which is provided for detecting foreign particles or voids in the outer insulation jacket of an electrical cable.

FIG. 2 is a diagramatic illustration of a portion of the system illustrated in FIG. 1, taken generally along line 2—2 in FIG. 1.

FIG. 3 is a diagramatic illustration of one way in which a laser beam of electromagnetic energy at a given wavelength passes through the insulation jacket of an electrical cable.

FIG. 4 is a diagramatic illustration of a controlled way in which the beam of electromagnetic radiation passes through the insulation jacket utilizing an index matching arrangement constructed in accordance with the present invention.

FIGS. 5 and 6 are schematic illustrations of further index matching arrangements constructed in accordance with the present invention.

FIG. 7 is a diagramatic illustration of a foreign particle/void detecting system constructed in accordance with a second embodiment of the present invention.

FIG. 8 is a diagramatic illustration of a cable inspection system and particularly one which scans a moving cable with a focused FIR laser beam.

DETAILED DESCRIPTION AND PREFERRED EMBODIMENTS

Turning now to the drawings, wherein like components are designated by like reference numerals throughout the various figures, attention is specifically directed to FIG. 1 which illustrates a system 10 constructed in accordance with the present invention and generally designated by the reference numeral 10. As stated previously, this system is provided for detecting foreign particles or voids in the outer insulation jacket of an electrical cable which is generally indicated at 12. This insulation jacket, indicated at 14, is constructed of a material having a known index of refraction and an absorption coefficient sufficient to pass electromagnetic radiation of a given wavelength. As will be seen, the foreign particles and voids which can be detected are of sizes within a range depending upon the wavelength selected.

In a preferred and actual working embodiment of the present invention, insulation jacket 14 is conventional cross-linked polyethylene extruded insulation which is especially made for power cable conductors and which displays an index of refraction of approximately 1.5 and an absorption coefficient less than ($<$)1 cm$^{-1}$ when a laser beam of far-infrared radiation having a wavelength of 119 μm is passed therethrough. This cross-linked polyethylene provides excellent dielectric and mechanical properties for electric power transmission and distribution applications at very low costs as compared with alternative types such as high-pressure oil-filled paper insulation. The polyethylene is formed by the extrusion of mixtures of plastic resins around a central metallic conductor generally indicated at 16 in FIG. 1. The extruded insulation medium is cross-linked typically by subjecting it to high-pressure steam. However, the mixing and cross-linking processing may produce contaminants and voids which are centers for the deterioration of the insulation's dielectric integrity by treeing processes leading to power cable failure and, hence, it is necessary to detect these contaminants and voids before they lead to failure.

In order to detect the voids or contaminants located within insulation jacket 14 of cable 12, overall system 10 includes an arrangement 18 for producing at its output a laser beam of electromagnetic radiation at a given wavelength, the beam being generally indicated at 20. This arrangement which will be discussed in more detail hereinafter, is preferably one capable of producing a far-infrared laser beam at a number of different wavelengths within the far-infrared spectrum, that is, between 70 micrometers and 2000 micrometers, and specifically one having a wavelength of approximately 119 micrometers. This particular type of laser beam is selected for a number of reasons. First, polyethylene is practically transparent to this radiation. Second, it provides for detecting the typical sized voids found in the insulation jacket. Other reasons will be apparent hereinafter.

In addition to laser producing arrangement 18, system 10 includes an overall optical arrangement 22 which serves a number of purposes in the embodiment illustrated in FIG. 1. First, it utilizes a conventional wire-grid polarizer 23 for examining, and if necessary, correcting the polarization output of beam 20 to insure proper polarization thereof. Second, this optical arrangement utilizing a beam splitter 24 or other such means redirects beam 20 from its output path indicated at 25 along a path indicated at 26 which is incident to and at a predetermined orientation with cable 12.

As illustrated in FIG. 1, it can be seen that the lateral extent of the overall beam along incident path 26 is substantially equal to and in alignment with the outermost extent of cable insulation jacket 14. In this way, as will be seen below, electromagnetic radiation from beam 20 is directed into and through insulation jacket 14, above and below inner conductors 16.

As seen in FIG. 1, the electromagnetic radiation which comprises outer portions 30 of beam 20 is directed into and through insulation jacket 14 of cable 12 along incident path 26. In this regard, it is important to note that the radiation which passes through the insulation jacket unobstructed by voids or foreign matter within the jacket does so along predictable beam refraction paths indicated generally by the arrows 34. These paths may be readily predicted by those with ordinary skill in the art because the index of refraction of jacket 14 is known and the incident beam is sufficiently controlled for controlling its angle of entry (incident angle) within the jacket. On the other hand, the electromagnetic radiation which impinges on a foreign particle or void, for example void 36 illustrated in FIG. 1, as it passes through jacket 14 is scattered thereby along predictable scattering paths including paths different than the refraction paths 34. Two such paths are indicated at 38 and 40.

In order to monitor the presence or absence of a void 36 or a foreign particle, system 10 includes conventional devices 42 and 43 for detecting electromagnetic radiation at a wavelength identical to that of beam 20. These devices, which will be discussed in more detail hereinafter, are respectively positioned in alignment with scattering paths 38 and 40 as illustrated, for detecting that portion of the scattered electromagnetic radiation directed along these paths. Each detecting device may include a suitable lens 44 for aiding in capturing scattered radiation. So long as the amount of radiation which is scattered along paths 38 and 40 is significantly greater than the background radiation also passing along the same paths, detectors 42 and 43 can easily discriminate between the presence and absence of a void or foreign particle. Background radiation may be defined as that radiation of the same wavelength, i.e. radiation from beam 20 which is not scattered radiation from a void or foreign particle. This would include radiation passing through the insulation jacket unobstructed by voids or foreign particles as well as radiation which is reflected off of the outer surface of jacket 14 or the outer surface of inner cable 16. As stated previously, the paths taken by the refracted radiation or, at least, substantially all of the refracted radiation are predictable and, hence, the scattering path 38 or 40 which is different than the refraction path can be readily selected. Moreover, as will be discussed below, these scattering paths can be selected so that they are different than any reflecting paths.

As just stated, in order to minimize background noise, each of the detection devices 42 and 43 must be located on a scattering path which is different than any of the refraction paths 34 and preferably different than the reflection paths defined by radiation from beam 20 reflecting off of the outer surface of insulation jacket 14 or inner conductors 16. As will be discussed below, in order to further minimize background noise, the scattering paths selected in one embodiment are not only different than the refraction paths and reflection paths but are specifically selected so as not to extend entirely within any plane which includes the incident path 26 of beam 20. In this way, the possibility of selecting a scattering path which coincides with an unpredicted refraction or reflection path is substantially minimized, if not eliminated.

From the foregoing, it should be obvious that there must be a sufficient number of scattering paths resulting from the impingement of radiation from beam 20 on a void or foreign particle in insulation jacket 14 in order to select particular paths meeting the requirements discussed above. Ideally, if the impinged radiation is scattered isotropically, the appropriate scattering paths can be readily selected to minimize if not completely eliminate background noise of the type described. In this regard, scattering of light from spherical particles has been treated extensively in the past. Mathematical formulations for both the intensity and polarization of scattered electromagnetic radiation are available in the technical literature for a single spherical particle and also for groups of such particles. As a general rule, it has been found that spherical voids or foreign particles having an average size (average diameter) which is approximately equal to the wavelength of radiation impinging on its surface will scatter the radiation isotropically. For wavelengths of light much larger than the average diameter of the scattering particle $(D/<<1)$ the intensity distribution is symmetrical about the plane through the center of the sphere at right angles to the direction of propagation of the incident light. As the radius of the sphere is increased, more light is scattered in the forward direction than in the opposite direction. When the diameter of the sphere is very large compared to wavelength $(D/\lambda >> 1)$ most of the incident light is forward-scattered. In actual practice, the voids to be detected are not spherical but more or less elliptical in shape which slightly changes the character of the scattered field. Nevertheless, the fact that they are not perfectly spherical in shape will not significantly alter the predicted scattering patterns.

From the foregoing, it should be apparent that there is one possible limitation which results from relying on scattering pattern which is isotropic or somewhat isotropic for selecting the appropriate scattering paths. Specifically, as stated, the voids or foreign particles to be detected must be matched with the wavelength of impinging radiation so that the two are substantially equal. However, there is another limitation relating to the penetrability of specific insulating materials by specific electromagnetic radiation. Fortunately, the most commonly used insulating material for power cables is polyethylene, as stated, and this particular material is practically transparent to far-infrared laser radiation. Accordingly, in a preferred and actual working embodiment of the present invention, laser beam 20 is a far-infrared beam when insulation jacket 14 is polyethylene. This, of course, limits the size of voids or foreign particles which produce an isotropic or near isotropic pattern to a size approximately equal to the particular wavelength of far-infrared radiation impinging the particles. Actually, it has been found that for particular wavelengths $\lambda$ within this far-infrared spectrum, the size of voids or foreign particles which can be accurately detected lies within a range between $\lambda/6$ and $2\lambda$.

In view of the foregoing, it should be readily apparent that the particular voids or foreign particles to be detected produce a scattering pattern sufficiently extensive so that scattering paths meeting the requirements discussed previously can be readily selected. As illustrated in FIG. 1, the scattering path 40 is located in front of cable 12, that is, in the backward direction with respect to the incident beam along path 26. This, of course, places detector 43 in front of the cable, that is, in the backward direction with respect to the incident beam. As a result, this detector is clearly outside the path of refracted radiation (paths 34) and radiation which might be reflected off either the inner conductors 16 or the outer surface of jacket 14.

The only possible types of background radiation which might reach detector 43 would be radiation reflected towards the detector from the inner cables and radiation which might be scattered from a relatively rough outer surface of the insulation jacket. Regarding this first possibility, while not shown, the center of radiation from beam 20 may be eliminated, and therefore the possibility of inner conductor 16 reflecting radiation back towards detector 43 from inner conductor 16 is minimized, if not eliminated. With regard to this second possibility, the scattered background radiation resulting from the rough surface of the insulation jacket may be readily measured by the RMS height of the surface. In the case of cable 12, it is anticipated that this height will be considerably less than the wavelength of impinging radiation and, hence, relatively smooth. Moreover, it can be assured that the scattering from a relatively smooth surface is mostly specular in nature and hence passes behind the cable, that is, in a forward direction with respect to the incident beam.

It is, however, desirable to utilize more than one detector and, in fact, it is desirable to locate a detector behind the cable, that is, in a forward direction with respect to the incident beam. Therefore, the scattering path selected, for example path 38, must be one which does not receive refracted background radiation or specular background radiation. As stated previously, this scattering path can be readily selected to be outside of the path of predicted refractive radiation as well as predicted reflected radiation. However, in order to minimize the possibility that scattering path 38 coincides with an unpredicted refraction path (or reflection path for that matter), path 38 is vertically inclined, that is, at an acute angle $\theta$ $\theta(v)$ vertically with the incident beam, as seen in FIG. 1, but more importantly it should be horizontally inclined, that is, at an acute angle $\theta(h)$ horizontally with the incident beam, as seen in FIG. 2. In other words, in one embodiment of the present invention, scattering path 38 is selected so as not to extend entirely within any plane which includes the incident path of beam 20, that is, path 26. In this way, the possibility of refracted radiation or reflected radiation from detector 42 is minimized, if not eliminated, unless of course the radiation either impinges on a foreign particle or non-homogeneous section in the insulation jacket or on an irregular surface comprising part of either innner conductors 16 or jacket 14. Obviously, detector 43 can be located in the same vertically/horizontally inclined manner.

From the foregoing, it should be quite apparent that the scattering paths used for detecting scattered radiation from voids or foreign particles can be readily selected when the scattering pattern is isotropic or near isotropic. On the other hand, when the scattering pattern is more limiting, it becomes more difficult to select appropriate scattering paths. However, it is to be understood that the present invention is not limited to the detection of particular voids using a particular radiation beam which together provides isotropic or near isotropic scattering patterns. However, once a particular material making up insulation jacket 14 is known and an electromagnetic radiation beam within a compatible spectrum is chosen, the scattering pattern of voids or foreign particles within a particular size range, within practical limits, can be readily determined. Once this pattern is determined and both the predicted refraction and reflection paths are plotted, scattering paths 38 and 40 as well as other scattering paths which meet the requirements discussed above can be readily selected. For example, based on actual scattering pattern in a working embodiment of the present invention, forward scattering path 38 was selected such that $\theta(V)$, that is, the vertical acute angle between the scattering path and incident path 26, was approximately equal to 0° and $\theta(h)$, that is, the horizontal acute angle, was approximately equal to 20°. However, it is to be understood that $\theta(V)$ and $\theta(h)$ are not limited to these particular angles.

The detectors themselves, like beam producing arrangement 18 may be conventional. Obviously, it will be necessary to select a device adapted to detect radiation at the wavelength of beam 20. In this regard, the size range of particles to be detected can be enlarged by generating a laser beam made up of a number of wavelengths, comparatable of course with cable 12 from both an index of refraction standpoint as well as absorption coefficient standpoint. Obviously, the detector then has to be selected to detect this multi-wavelength radiation.

Once the detected radiation reaches a predetermined threshold level at a given detector, for example detector 42 (or 43), the latter will generate an output signal. The threshold level of detector 42 (or 43) is selected to indicate the presence of a void or foreign particle in the size range of interest and the signal at its output will represent such a void or foreign particle and may be used in a number of ways. For example, this output can be used merely to drive visual or permanent readouts with or without an appropriate alarm. On the other hand, it could be used in an overall feedback arrangement not only for monitoring the insulation jacket for voids and foreign particles, but also for regulating the process which produces the jacket for minimizing or eliminating these voids and contaminants. In this regard, system 10, as described, is especially suitable for use in line with the manufacturing of cable 12. More specifically, radiation beam 20 could be directed into insulation jacket 14 along incident path 26 in the manner described above as cable 12 moves axially (out of the paper in FIG. 1) just off the production line.

In view of the foregoing, it should be readily apparent that system 10 is provided for detecting voids and-/or foreign particles or particular sizes in the outer insulation jacket of an electrical cable, which jacket has a known index of refraction and an absorption coefficient sufficient to pass electromagnetic radiation of a given wavelength. As stated previously, this is accomplished by producing a laser beam of electromagnetic radiation at the given wavelength and directing this beam into the insulation jacket along a path incident to and at a predetermined orientation with the cable. In this way, a portion of the beam which passes through the insulation jacket unobstructed by voids or foreign matter within the jacket does so along predictable beam refraction paths as does a portion which is reflected off of the outer surface of the insulation jacket as well as the outer surface of the inner conductors. Moreover, any portion of the beam which impinges on one of the voids or foreign particles as it passes through the jacket is scattered thereby from predictable scattering paths including scattering paths different than the refraction paths or reflection paths. In this way, a suitable device for detecting electromagnetic radiation of the given wavelength may be positioned in alignment with one of these different scattering paths to provide indicative outputs for a void or foreign particle as discussed above. There is however one area in this particular system, as described, which requires improvement. Specifically, as the beam of radiation initially enters insulation jacket 14 from the ambient surrounding, it passes from air (having an index of refraction "n" equal to 1.0) to a material more than likely having a different index of refraction (specifically a refractive index equal to 1.5 when the material is cross-linked polyethylene insulation, as stated previously).

Substantially all of the radiation from beam 20 which enters insulation jacket 14 does so at different angles (since the jacket is cylindrical) which causes it to be refracted in different ways as it enters the jacket. This, in turn, means that the two sections 30 of beam 20, as illustrated in FIG. 1, are not uniformly passed through the insulation jacket 14 above and below inner conductors 16. This is best illustrated in FIG. 3 which shows the ray paths of a far-infrared laser beam inside the cable jacket of cylindrical cross-section. This illustration was obtained by means of ray-tracing, treating the beam as having a uniform intensity and passing directly from air (N=1.0) to cross-linked polyethylene insulation (n=1.5). Only the transmitted rays are shown. Rays striking the inner conductors are eliminated. Moreover, while not shown, radiation from the beam will be reflected at the various surfaces. However, for purposes of the present discussion, these reflected rays have been ignored.

As illustrated in FIG. 3, the insulation jacket acts like a focusing lens, with the result indicating that large regions are not illuminated at all. Results further indicate that a minimum of three far-infrared laser beams are needed to provide a complete coverage of a cable with a cylindrical geometry. However, in order to pass the rays more uniformly through insulation jacket 14, system 10 may include a refractive index matching arrangement which is generally indicated by the reference numeral 50 in FIGS. 1 and 4. As illustrated in FIG. 4, which also includes a ray tracing similar to FIG. 3, arrangement 50 includes a solid block of a material having substantially the same index of refraction as the insulation jacket, specifically polyethylene having an index of refraction of approximately 1.50 in an actual working embodiment. This block of polyethylene material, which is generally designated at 52, includes an open-ended cylindrical passage 54 which is slightly greater in diameter than insulation jacket 14 and which extends from one end of the block to an opposite end.

As seen in FIG. 4, block 52 is positioned concentrically around insulation jacket 14 such that the two together define an annular space 56 therebetween. This space will be discussed hereinafter. In the meantime, it is to be noted that block 52 also includes a front side 58 defining a substantially planar, frontal-most surface 60 which is substantially parallel with the axis of passage 54 and which extends from one end thereof to the other. The block also includes an opposite backside 62 which may have a plurality of angled surfaces 64, actually two in the embodiment illustrated, each extending in a plane which is at an acute angle with frontal-most surface 60. As will be seen hereinafter, the angle of these latter surfaces 64 depend upon the positions of the selected scattering paths and corresponding detection devices.

In addition to polyethylene block 52, arrangement 50 includes a liquid substance 66 located within and filling annular space 56. This liquid substance is specifically selected to have an index of refraction approximately equal to the index of refraction of insulation jacket 14 and an absorption coefficient which is at most approximately equal to the absorption coefficient of the jacket, at the operating wavelength of beam 20. As stated previously, insulation jacket 14 when constructed of the aforediscussed polyethylene material has an index of refraction equal to 1.50. It also has an absorption coefficient which is less than 1 cm$^{-1}$. There are a number of liquids having compatible refractive indices and exhibiting extremely low absorption characteristics, particularly at 119 micrometers laser wavelength, the preferred operating wavelength of the present invention. In this regard, three such substances are illustrated in Table I below. The absorption coefficient of these liquids have been measured at 119 micrometer wavelengths, by passing the laser radiation through an absorbing cell with two polyethylene windows. Table I specifically lists the percent of transmission of the 119 micrometer radiation through the liquid filled cell with an absorption coefficient of 0.48 cm. Also included in Table I are the measurements of the indices of a few fluids at both the 0.63 micrometer and 119 micrometer laser wavelengths. The indices of refraction for these liquids listed in Table I are approximately the same at these two wavelengths.

TABLE I

| Measurements of Transmission and Index of Refraction | | |
|---|---|---|
| Liquid | Transmission % | Index of Refraction |
| Welch Duo Seal Pump Oil | 62.5 | 1.49 |
| #9534 Oil (Red) | 48.5 | 1.48 |
| Sears Machine Oil (Light) | 66.5 | 1.49 |

In order to maintain liquid substance 66 within annular space 56, arrangement 50 includes suitable sealing means (not shown) such as rubber O-rings located at opposite ends of the annular space.

Having described arrangement 50, attention is now directed to the manner in which it functions to more uniformly pass the radiation from beam 20 to insulation jacket 14. As illustrated in FIG. 4, frontal-most surface 60 is positioned normal to incident path 26 and, hence, normal to the incident rays from beam 20. As a result, the rays passing into block 52 from front surface 60 are not refracted in a significant way. Moreover, since liquid substance 66 has approximately the same index of refraction as block 58 and insulation jacket 14 and since it extends entirely across the otherwise empty space (annular space 56) it in effect eliminates this space or at least it eliminates it as far as the radiation is concerned. More specifically, as the radiation passes across this gap it is not refracted to any significant degree and hence passes through the insulation jacket along essentially the same straight line path along which it entered block 52. In this way, much more of the insulation jacket receives radiation from beam 20 than is the case with respect to FIG. 3.

Nevertheless, it should be quite apparent that part of the backside of the jacket, that is, the section of jacket 14 located behind conductors 16, will not be exposed to radiation from beam 20 and, hence, for complete coverage a second beam is required, for example one having an incident path normal to path 26. In any case, it should be apparent from FIG. 4 that the radiation exiting angled surfaces 64 is refracted as indicated at 34' but is refracted along predictable paths since the index of refraction of block 52 is known as well as the angles at which the radiation impinges surfaces 64 as the radiation leaves the block. For the same reasons, the paths of reflection including for example those generally indicated at 68 are predictable.

FIG. 4 not only illustrates refraction paths 34' and reflection paths 68, but also two scattered rays from a void 70 located within insulation jacket 14. The two rays selected (actually paths) are indicated at 72 and each extends at an angle of 30° to the local incident ray. In this regard, it is to be noted that each of the surfaces 64 is cut at 30° to the horizontal, that is, 30° to the direction of the incident rays (which is the same as previously recited incident path 26), so that the scattered rays 72 are normal to these cut surfaces. In this way, the scattered rays pass out of block 52 without being refracted and, hence, can be more accurately predicted for properly aligning their associated detectors, that is, the detectors which would be aligned with these scattering paths.

The particular index matching arrangement just described is one which includes a single frontal-most incident surface (surface 60) and only two angled exit surfaces (surfaces 64). It is to be understood that a similar arrangement could be utilized including more than one frontal-most incident surface, more than two angled exit surfaces and an exit surface or surfaces which are parallel to the frontal-most entry surfaces. For example, FIG. 5 illustrates diagramatically an arrangement 50' which may be identical to arrangement 50, with one exception. More specifically, arrangement 50' may include a frontal-most incident surface 60' and two angled exit surfaces 64'. However, in addition, arrangement 50' may include an exit surface 74 which is located between angled surfaces 64 and which is parallel to incident surface 60'. On the other hand, arrangement 50'', as illustrated in FIG. 6, may be provided. This latter arrangement includes two frontal-most incident surfaces 60'' which are located 90° from one another, a number of angled exit surfaces 64'' and a parallel exit surface 74'' associated with each incident surface.

Having described system 10 and index matching arrangements 50, 50' and 50'' which can be used in system 10, attention is now directed to FIG. 7 which illustrates a modified void or foreign particle detecting system generally indicated by the reference numeral 80. This latter system may include a laser source identical to previously recited arrangement 18 which, as seen in FIG. 7, may include a far-infrared laser 82 and associated $CO_2$ pump laser 84 which cooperate with one another and with a beam reflector 86 and lenses 88 and 90 for producing a collimated far-infrared laser beam 92. A beam splitter indicated at 94 is utilized to split beam 92 into two beams 92a and 92b. Beam 92a is allowed to pass along its original path into and through cable 12 and index matching arrangement 96 which is located around the cable and which may be identical to previously described arrangement 50''. However, in the embodiment illustrated, index matching arrangement 96 includes a fewer number of angled surfaces. Beam 92b is ultimately directed into and through cable 12 and index matching arrangement 96 at an angle 90° from beam 90a by means of two further beam splitters (actually mirrored surfaces) 98 and 100.

System 80 also includes detection devices 102 which may be identical to previously recited detection devices 42 and 43. As illustrated in FIG. 7, each of the detection devices 102 includes an associated polyethylene lens 104 and is positioned with its lens on a radiation scattering path 106 which is normal to the corresponding angle surface. The way in which system 80 operates as thus far described is identical to the way in which system 10 operates, as described previously. However, it should be quite apparent that the entire cross-section of insulation jacket 14, within the bounds (width) of beams 92a and 92b is exposed to radiation. Moreover, instead of utilizing a single detector or two detectors as illustrated with respect to system 10, system 80' utilizes four detectors. Obviously, any number, within practical limits, could be utilized.

System 80 is also shown to include a radiation absorbing device 108 and associated collecting lens 110 as well as a laser monitor 112 and associated collecting lens 114. More specifically, absorber 108 may be utilized for absorbing the refracted radiation from beam 92b while monitor 112 may utilize the refracted radiation from beam 92a for regulating the overall laser producing arrangement. These latter devices, specifically absorber 108 and monitor 112 may be conventional along with the overall laser producing arrangement and detectors.

As stated previously, in most situations, the voids/foreign particle detection system of the present invention will be used to detect voids or foreign particles in a power cable having an insulation jacket constructed of specific polyethylene material of the type described above. When this is the case, the detection system in its peferred embodiment includes a conventional arrangement for producing an FIR laser beam of a particular wavelength or wavelengths and conventional devices for detecting radiation at that wavelength or wavelengths. In this preferred embodiment, one wavelength selected at 119 microns and the size of the particles to be detected are between 50 microns and 2000 microns as discussed previously.

As just stated, the laser beam may be produced conventionally. For example, by means of optical pumping of a low pressure polar molecular gas, about 300 laser oscillations in the submillimeter wave region between 34 micrometers and 1.8 millimeters have been reported. Numerous molecular species have been found to yield laser action in the desired far-infrared wavelength band. Most of these laser lines correspond to rotational transitions in an excited vibrational state which has the spectral coincidence with a specific vibrational-rotational transition of $CO_2$ laser line. Two of the most efficient molecular gases are methylalcohol and methylfluoride.

A typical FIR laser system uses a grating-tuned $CO_2$ laser as a pump source and produces a submillimeter wave output of the order of 100 mW in the CW mode or more than several kilo watts in the pulsed mode. The main part of the FIR laser system is a resonator which is filled with specific active polar molecules to a pressure of 10 to 1000 m-Torr and is axially pumped by the $CO_2$ laser radiation. The most commonly used resonator type is a meter-long tunable length, near semi-confocal hole-coupled, Fabri-Perot resonator of large Fresnel number (N greater than 1). This type of laser system is shown in FIG. 7 as part of the overall detection system 80.

The output from an optically pumped submillimeter wave laser has natural tendencies to be linearly polarized in either the same orientation with or perpendicular to the pumped field depending on the types of transition involved. This is due to the fact that the dipole moments for both the pump transition and the lasing transition are always either perpendicular or parallel to the total angular momentum victor of the lasing molecule. The lasing medium has no discharge as required for most conventional lasers. Therefore, it can be made as stable as the pump laser which has already reached its state of maturity. Strong CW far-infrared laser lines optically pumped by a line-selecting $CO_2$ are well known and hence will not be recited herein.

For a given molecular gas, a number of FIR laser transitions can be obtained by varying the wavelength of the $CO_2$ laser pump. The wavelength of the FIR laser output can be easily estimated with about 1% accuracy by using the FIR laser resonator as a self-scanning interferometer, or by using an external far-infrared interferometer, which uses fine metal-mash mirrors, to increase the accuracy to about 1 part in $10^4$. A still higher accuracy of one part in $10^6$ or better can be achieved in frequency measurement by mixing the FIR signal with the harmonics of an accurately monitored tunable microwave source in a point contact diode.

In the design of the FIR laser resonator, the mirror diameters must be made sufficiently large to avoid excessive difraction losses. The Fresnel number of the resonator should be greater than 1.5 at the longest wavelength of interest. The curvature of the mirrors should also be chosen with care. For instance, the pump beam may not be sufficiently absorbed in a confocal or semi-confocal resonator as the pump beam is refocused onto the coupling hole and reflected out of the resonator after only a few bounces in the resonator.

It is to be understood that the specific beam producing arrangement just described has been provided for examplary purposes only and it is not intended to limit the present invention nor to be a full and complete discussion of FIR lasers and $CO_2$ laser pumps. Those with ordinary skill in the laser art can readily provide an appropriate laser producing arrangement.

For the detection of radiation in the submillimeter wave region, there exists a variety of liquid helium cooled as well as room temperature detectors. For wavelengths less than 170 micrometers, galium doped germanium photoconductors are good choices. For $\lambda$ greater than 150 micrometers, either indium antimonide hot electron bolometers or galium arsonide photoconductors should be considered. These low temperature photoconductors have not only extremely high sensitivity but also fast time response typically less than 10 nanoseconds. For CW signals, it may be more convenient to use the slower room temperature thermal detectors such as Golay cells, vacuum thermal couples or flake thermister. These room temperature detectors are less sensitive, but still have NEP's lower than $10^{-9}$ watts per Hz one-half band widths. The actual operating temperatures and corresponding time responses of these detectors are known and hence will not be set forth herein.

The specific detectors just discussed, like the previous specific laser producing arrangement discussed above, have been provided for examplary purposes only and are not intended to limit the present invention. In addition, this discussion is not intended as a full and complete discussion of the recited detectors since those with ordinary skill in the laser and laser detection art could readily provide the appropriate detector of the present invention, as stated previously.

The system described in FIG. 1 utilizes a stationary far-infrared laser beam whose cross-sectional area is sufficiently large to fully illuminate the cable cross-section. In some cases, it may be desirable to increase its laser power density at the defect site in order to enhance the scattered signal power. To achieve this enhancement, a system as shown in FIG. 8 may be employed. A combination consisting of a curved focussing mirror 121 and a flat scanning mirror 120 is used to focus this laser beam into the cable insulation through the index matching block 52 and scan the focused beam across the cable cross-section while the cable is in motion. A far-infrared detector 42 is placed off axis from the beam and, as stated previously, is oriented at a predetermined position to collect the off-axis scattered far-infrared laser radiation from the defects inside the polyethylene insulation, and does not collect energy from the primary beam 34 in the forward direction. The detection output is fed into a signal processor 123 which can register the occurrence of defect signals greater than a predetermined threshold level, and provide a permanent record of the signal amplitude associated with the defects. Such a system, as illustrated in FIG. 8, is also suitable to perform real-time inspection and manufacturing control of cable insulation quality.

The signal processor 123 can also receive signals from the scanning mirror 121 and from a length monitor, indicated schematically as 122, to provide simultaneous information on the location of the defect.

What is claimed is:

1. A system for detecting foreign particles or voids in the outer insulation jacket of an electrical cable, said insulation jacket being cylindrical in cross-sectional configuration and constructed of a material having a known index of refraction and an absorption co-effeicient sufficient to pass electromagnetic radiation of a given wavelength and said foreign particles and voids being of sizes within a predetermined range, said system comprising;
   (a) means for producing a laser beam of electromagnetic radiation at said given wavelength;
   (b) means for directing said beam into said insulation jacket along a path incident to and at a predetermined orientation with said cable such that
      (i) any portion of said beam which passes through said insulation jacket unobstructed by voids or foreign matter within said jacket does so along predictable non-impinging paths, and
      (ii) any portion of said beam which impinges one of said foreign particles or voids as it passes through said jacket is scattered thereby along predictable scattering paths including paths different than said non-impinging paths;
   (c) a refractive index matching arrangement for minimizing the refraction of said beam as the latter initially passes into and out of said insulation jacket, said arrangement including
      (i) a solid body having a planar frontside, a backside, opposite ends and the same index of refraction as said insulating jacket, said body also including an open ended cylindrical passage which is slightly larger than said jacket and which extends from one of said opposite ends to the other parallel with said planer frontside, said body being adapted for positioning concentrically around said jacket such that said jacket and block together define an annular space there between and such that the frontside of said block presents a normal surface to said beam before the latter enters said insulation jacket,
      (ii) a liquid located within and filling said annular space, said liquid having an index of refraction approximately equal to that of said insulating jacket and an absorption co-efficient approximately equal to that of said jacket at said given wavelength, and
      (iii) means for sealing said liquid within said annular space; and
   (d) means for detecting electromagnetic radiation of said given wavelength, said means being positioned in alignment with at least one of said different scattering paths, whereby to detect any of said scatter electromagnetic radiation which is directed along said last-mentioned scattering path.

2. A system according to claim 1 wherein said given wavelength is within the far-infrared band of 70 microns to 2000 microns.

3. A system according to claim 1 wherein said wavelength is approximately 119 μm.

4. A system according to claim 1 wherein said insulation jacket is constructed of polyethylene material.

5. A system according to claim 4 wherein said polyethylene has an index of refraction of about 1.5 and wherein said detecting means is positioned in alignment with said last-mentioned scattering path which is located at an angle of about 20° horizontally with the incident path of said beam.

6. A system according to claim 1 wherein
   (a) said laser beam is a beam of far-infrared radiation having a wavelength of about 119 μm; and
   (b) said insulation jacket is constructed of polyethylene material having an index of refraction of about 1.5 and an absorption coefficient less than 1 cm$^{-1}$ at said wavelength.

7. A system according to claim 1 wherein the outer surface of said insulation jacket is sufficiently smooth so to substantially eliminate any back scattering of electromagnetic radiation in front of said cable and wherein said detecting means and its associated scattering path are located in front of said cable at an acute angle with the incident path of said beam.

8. A system according to claim 1 wherein the outer surface of said insulation jacket is sufficiently smooth so as to cause some of the electromagnetic radiation from said beam to be reflected off of said smooth surface along predictable paths passing beyond and behind said cable and wherein said detecting means and its associated scattering path is located behind said cable and out of any of said reflecting paths.

9. A system according to claim 1 wherein the foreign particles and voids to be detected are shaped and sized relative to said given wavelength such that said beam portion impinging on one of said particles or voids is scattered substantially isotropically.

10. A system according to claim 9 wherein said last-mentioned scattering path is located behind said cable and is selected so as not to extend entirely within any plane which includes the incident path of said beam.

11. A system according to claim 1 wherein the average size of said particles to be detected is between about one-sixth said given wavelength and twice said given wavelength.

12. A system according to claim 1 wherein said detecting means includes means for producing an output signal when the amount of said scattered radiation detected reaches a predetermined threshold level at any given instant during operation of said system, whereby to indicate the presence of a void or foreign particle.

13. A system according to claim 1 including means located behind said cable and adapted to capture and then absorb at least a portion of said unobstructed beam portion.

14. A system according to claim 1 including means adapted to capture at least a portion of said beam of electromagnetic radiation for monitoring its intensity and wavelength.

15. A system according to claim 1 wherein
   (a) said beam directing means includes
      (i) beam splitting means for producing a second beam from said beam, and
      (ii) means for directing said second beam into said insulation jacket and matching means along a second different path incident to and at a predetermined orientation with said cable such that
         (1) any portion of said second beam which passes through said insulation jacket unobstructed by voids or foreign matter within said jacket does so along predictable second beam refraction paths, and
         (2) any portion of said second beam which impinges one of said foreign particles or voids as it passes through said jacket is scattered thereby along predictable second scattering paths including paths different from first-mentioned and second beam refraction paths and said first-mentioned beam scattering paths; and
   (b) said system includes means for detecting electromagnetic radiation at said given wavelength, said means being positioned in alignment with at least one of said second different scattering paths, whereby to detect any of said scattered electromagnetic radiation which is directed along said last-mentioned scattering path.

16. A continuous monitoring system for detecting foreign particles or voids in the outer cylindrical insulation jacket of a power cable as the latter moves along a fixed path, said insulation jacket being constructed of polyethylene material having a predetermined index of refraction and said foreign particles or voids being of sizes within a predetermined range, said system comprising:
   (A) a refractive index matching arrangement including
      (i) a substantially solid block of polyethylene material having the same index of refraction as said insulating jacket and including
         (a) an open-end cylindrical passage slightly larger than said insulating jacket extending from one end of said block to an opposite end, said block being adapted for positioning in said fixed path such that said power cable passes concentrically through said passage as it moves along said path, said insulating jacket and block together defining an annular space therebetween,
         (b) a first front side having a substantially planner outer surface substantially parallel with said passage and extending from one end thereof to the other,
         (c) a first, opposite back side having a plurality of outer surfaces, one of which is parallel with said first front side surface and the other of which extend at predetermined angles with said parallel back side surface,
         (d) a second front side having a substantially planner outer surface normal to said first front side surface and substantially parallel with said passage and extending from one end thereof to the other, and
         (e) a second opposite back side having a plurality of outer surfaces, one of which is parallel with said second front side surface and the others of which extend at predetermined angles with said second parallel backside surface,
      (ii) a liquid located within and filling said annular space, said liquid having an index of refraction approximately equal to that of said insulating jacket and an absorption coefficient approximately equal to that of said jacket at a given wavelength of electromagnetic radiation in the far-infrared band, and
      (iii) means for sealing said liquid within said annular space;
   (B) a far-infrared laser source for producing a laser beam having a frequency in the far-infrared band and a width approximately equal to the outer diameter of said insulation jacket;
   (C) an optical arrangement including
      (i) means for splitting said beam into two beams,
      (ii) means for optically directing one of said two beams so as to impinge said first front side surface of said polyethylene block at an angle normal thereto and in alignment with said power cable, and
      (iii) means for optically directing the other of said two beams so as to impinge said second front side surface of said polyethylene block at an angle normal thereto and in alignment with said power cable; and
   (D) a plurality of far-infrared detector means, each of which is located a predetermined distance from and along a line normal to a corresponding one of said angled surface of said polyethylene block for detecting any far-infrared radiation passing thereto along said line.

17. A system according to claim 1 wherein said backside includes a plurality of planar sections, at least one of which is located in a plane extending at an angle with said planar frontside, said one section being positioned normal to said one scattering path when said body is in said concentric position.

18. A system according to claim 1 wherein both said insulation jacket and said body are constructed of the same material.

19. In a system for detecting foreign particles or voids in a cylindrical object by passing a beam of electromagnetic radiation through said object, a refractive index matching arrangement for minimizing the refraction of said beam as the latter initially passes into and out of said object, said arrangement comprising:
   (a) a solid body having a planar frontside, a backside, opposite ends and the same index of refraction as said object, said body also including a cylindrical passage which is slightly larger than the diameter of said object and which extends between said opposite ends parallel with said planer frontside, said body being adapted for positioning concentrically around said object such that the outer elongated surface of said object and block together define an annular space there between and such that the frontside of said block presents a normal surface to said beam before the latter is to enter said object;
   (b) a liquid located within and filling said annular space, said liquid having an index of refraction approximately equal to that of said insulating jacket; and (c) means for sealing said liquid within said annular space.

20. An arrangement according to claim 19 wherein said backside include a plurality of planar sections, at least one of which is located in a plane extending at an angle with said planar front side.

21. An arrangement according to claim 19 wherein said backside includes a plurality of planar sections which are located in a plane extending at predetermined angles with said planar frontside.

22. A system according to claim 19 wherein both said object and said body are constructed of the same material.

* * * * *